US010703622B2

(12) United States Patent
Carapelli et al.

(10) Patent No.: US 10,703,622 B2
(45) Date of Patent: Jul. 7, 2020

(54) FUEL DISPENSER WITH A FUEL ANALYZER

(71) Applicant: Gilbarco Inc., Greensboro, NC (US)

(72) Inventors: Giovanni Carapelli, High Point, NC (US); Wayne McNinch, Greensboro, NC (US); Changzhong Jiang, Greensboro, NC (US)

(73) Assignee: Gilbarco Inc., Greensboro, NC (US)

( * ) Notice: Subject to any disclaimer, the term of this patent is extended or adjusted under 35 U.S.C. 154(b) by 45 days.

(21) Appl. No.: 15/876,921

(22) Filed: Jan. 22, 2018

(65) Prior Publication Data

US 2018/0209940 A1 Jul. 26, 2018

Related U.S. Application Data

(60) Provisional application No. 62/448,643, filed on Jan. 20, 2017.

(51) Int. Cl.
*B67D 7/34* (2010.01)
*G01N 29/024* (2006.01)
(Continued)

(52) U.S. Cl.
CPC .............. *B67D 7/342* (2013.01); *B67D 7/04* (2013.01); *B67D 7/3281* (2013.01); (Continued)

(58) Field of Classification Search
CPC ............ G01N 29/024; G01N 29/4427; G01N 33/2829; B67D 7/04; B67D 7/342; G01F 1/66; G01F 1/662
See application file for complete search history.

(56) References Cited

U.S. PATENT DOCUMENTS 3,104,355 A 9/1963 Holmes et al.
3,906,791 A 9/1975 Lynnworth
(Continued)

FOREIGN PATENT DOCUMENTS

| CN | 102374880 A | 3/2012 |
|---|---|---|
| WO | 2012123673 A1 | 9/2012 |
| WO | 2016016818 A1 | 2/2016 |

OTHER PUBLICATIONS

International Search Report and Written Opinion dated Apr. 6, 2018 in corresponding Patent Cooperation Treaty No. PCT/US2018/014692, all enclosed pages cited.
(Continued)

*Primary Examiner* — Timothy P. Kelly
(74) *Attorney, Agent, or Firm* — Nelson Mullins Riley & Scarborough, LLP

(57) ABSTRACT

A fuel analyzer for a fuel dispensing environment is provided including an ultrasonic transmitter configured to transmit an ultrasonic signal through a volume of fuel, an ultrasonic receiver configured to receive the ultrasonic signal, and processing circuitry. The processing circuitry is configured to receive an indication of transmission of the ultrasonic signal from the ultrasonic transmitter, receive an indication of receipt of the ultrasonic signal from the ultrasonic receiver, determine a time of flight of the ultrasonic signal, and determine a fuel purity based on the time of flight of the ultrasonic signal.

15 Claims, 6 Drawing Sheets

(51) Int. Cl.
*B67D 7/04* (2010.01)
*G01N 33/28* (2006.01)
*B67D 7/32* (2010.01)
*G01N 29/44* (2006.01)

(52) U.S. Cl.
CPC ....... *G01N 29/024* (2013.01); *G01N 29/4427* (2013.01); *G01N 33/2829* (2013.01); *G01N 2291/02818* (2013.01)

(56) References Cited

U.S. PATENT DOCUMENTS

| | | | |
|---|---|---|---|
| 4,109,524 | A | 8/1978 | Smith |
| 4,187,721 | A | 2/1980 | Smith |
| 4,491,025 | A | 1/1985 | Smith et al. |
| 5,040,577 | A | 8/1991 | Pope |
| 5,135,029 | A | 8/1992 | Anderson et al. |
| 5,345,979 | A | 9/1994 | Tucker et al. |
| 5,448,921 | A | 9/1995 | Cage et al. |
| 5,564,471 | A | 10/1996 | Wilder et al. |
| 5,630,528 | A | 5/1997 | Nanji |
| 5,877,416 | A | 3/1999 | Kapartis |
| 5,954,080 | A | 9/1999 | Leatherman |
| 6,009,761 | A | 1/2000 | Taylor et al. |
| 6,164,140 | A | 12/2000 | Kalinoski |
| 6,253,779 | B1 | 7/2001 | Nanji et al. |
| 6,435,204 | B2 | 8/2002 | White et al. |
| 6,748,793 | B2 * | 6/2004 | Rabinovich .......... G01N 29/024 340/632 |
| 6,935,191 | B2 | 8/2005 | Olivier et al. |
| 7,252,112 | B1 | 8/2007 | Imler et al. |
| 7,287,438 | B2 | 10/2007 | Van Cleve |
| 7,322,245 | B2 | 1/2008 | Gysling et al. |
| 7,472,606 | B2 | 1/2009 | Seddon et al. |
| 8,291,928 | B2 | 10/2012 | Reid et al. |
| 8,342,199 | B2 | 1/2013 | Deline et al. |
| 9,383,237 | B2 * | 7/2016 | Wiklund .................. G01F 1/34 |
| 9,428,375 | B2 | 8/2016 | Sabo et al. |
| 9,475,687 | B2 | 10/2016 | Deline |
| 9,718,666 | B2 | 8/2017 | Cornett |
| 10,173,885 | B2 | 1/2019 | Carapelli |
| 2004/0006409 | A1 | 1/2004 | Liljenberg et al. |
| 2004/0254462 | A1 | 12/2004 | Kawagishi et al. |
| 2005/0028610 | A1 | 2/2005 | Olivier et al. |
| 2005/0125170 | A1 | 6/2005 | Gysling et al. |
| 2009/0195260 | A1 | 8/2009 | Bell et al. |
| 2010/0139782 | A1 | 6/2010 | Deline et al. |
| 2013/0345994 | A1 | 12/2013 | Wiklund et al. |
| 2016/0167942 | A1 | 6/2016 | Cornett |
| 2018/0257925 | A1 | 9/2018 | Schultz et al. |

OTHER PUBLICATIONS

Anil Gupta and R.K. Sharma (2010). "A New Method for Estimation of Automobile Fuel Adulteration," Air Pollution, Available from: http://www.intechopen.com/books/air-pollution/a-new-method-for-estimation-of-automobile-fuel-adulteration, all enclosed pages cited.

R.K. Sharma and Anil Kumar Gupta (2011). "Low Cost Method for Testing Automobile Fuels," Vivechan International Journal of Research, vol. 2, all enclosed pages cited.

* cited by examiner

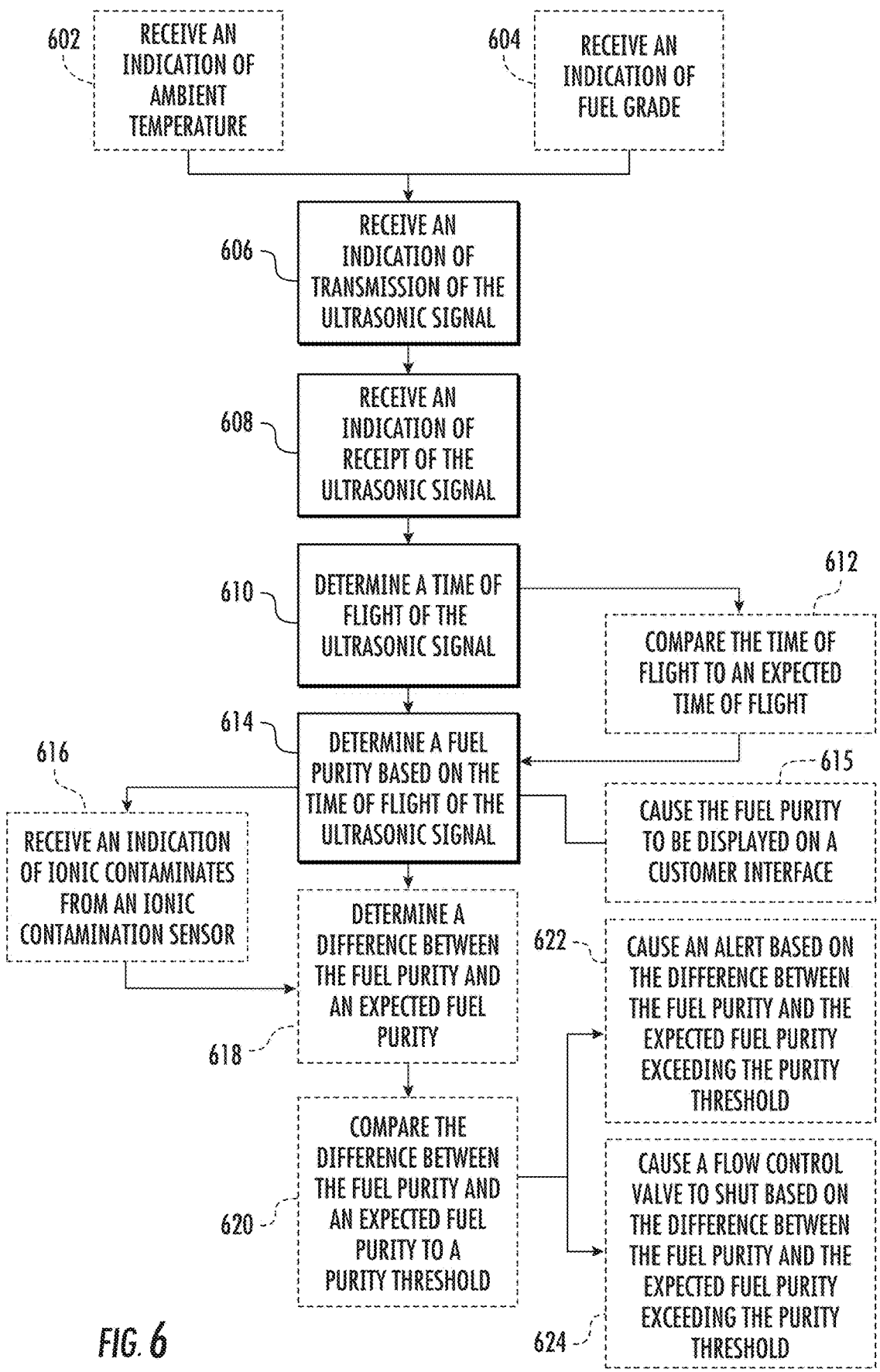

FUEL DISPENSER WITH A FUEL ANALYZER

PRIORITY CLAIM

This application is based upon and claims the benefit of U.S. provisional application Ser. No. 62/448,643, filed Jan. 20, 2017, which is relied upon and incorporated herein by reference in its entirety for all purposes.

BACKGROUND

The present invention relates generally to equipment used in fuel dispensing environments. More specifically, embodiments of the present invention relate to a fuel dispenser with a fuel analyzer.

Fuel adulteration is a major issue in many countries worldwide. Adulteration of fuel may include diluting a pure fuel grade, e.g. gasoline or diesel, with much cheaper additives, such as kerosene, in order to sell more quantity of fuel at regular fuel price. In some regions kerosene is subsidized by the government and given to families at a low price for cooking purposes. In these regions, the kerosene may be mixed with diesel or gasoline to dilute the fuel grade. In some instances, kerosene may make up to 30 percent of the fuel. This illegal practice has several negative impacts on society: tax evasion, damage to vehicle engines, fuel provider, e.g. oil company, reputation, and the like. Overall damages to one example nation's economy is about one billion dollars each year.

Adulteration may also occur in non-fraudulent ways, for example the mixing of water in fuel tanks after heavy rains. The water may enter the fuel tanks through vent leaks or other infrastructure issues. In another example, incorrect fuel grades may be inadvertently sold, for example by delivering E15 (15 percent ethanol) fuel into E85 (85 percent ethanol) tanks and vice-versa.

In an attempt to raise awareness of adulteration some dispensers have been equipped with a density display mounted on dispenser, showing the fuel density, since fuel density typically changes due to adulteration. However, these dispensers do not measure density, but are merely displaying a set value associated with the fuel grade.

Measuring density in a fuel environment may be generally characterized as a complex and expensive process. In some fueling environments, fast gas chromatograph with surface wave (SAW) detector may be utilized to determine the mass or chemical makeup of the fluid. However, this method has been implemented only in countries, such as Russia, where the expected temperature may change dramatically, e.g. become extremely cold. Thus causing a substantial change in the density and hence the 'value' of fuel delivered to the customer. In other fueling environments, such as in Canada, a method of automatic temperature compensation has been utilized. The automatic temperature compensation may be based on temperature detection and compensation 'tables' that would equalize the volume (so at very low temp, a less quantity of fuel is dispensed for a given price, calculated on volumetric base at ambient temperature). None of these methods is effective in detecting adulteration by fraud, infrastructure issues, or human error.

SUMMARY

The present invention recognizes and addresses various considerations of prior art constructions and methods. According to one aspect, the present invention provides a fuel analyzer for a fuel dispensing environment including an ultrasonic transmitter configured to transmit an ultrasonic signal through a volume of fuel, an ultrasonic receiver configured to receive the ultrasonic signal, and processing circuitry. The processing circuitry is configured to receive an indication of transmission of the ultrasonic signal from the ultrasonic transmitter, receive an indication of receipt of the ultrasonic signal from the ultrasonic receiver, determine a time of flight of the ultrasonic signal, and determine a fuel purity based on the time of flight of the ultrasonic signal.

In another example embodiment, a fuel dispenser is provided including a fuel nozzle configured to be connected to a vehicle fuel system, fuel piping configured to transfer fuel from at least one fuel storage tank associated with the fuel dispenser through the fuel nozzle into the vehicle fuel system, and a fuel analyzer. The fuel analyzer includes an ultrasonic transmitter configured to transmit an ultrasonic signal through a volume of fuel, an ultrasonic receiver configured to receive the ultrasonic signal, and processing circuitry. The processing circuitry is configured to receive an indication of transmission of the ultrasonic signal from the ultrasonic transmitter, receive an indication of receipt of the ultrasonic signal from the ultrasonic receiver, determine a time of flight of the ultrasonic signal, and determine a fuel purity based on the time of flight of the ultrasonic signal.

In a further example embodiment, a fuel environment is provided including a fuel storage tank configured to store fuel, a fuel dispenser configured to dispense the fuel from the fuel storage tank, and a fuel analyzer disposed between the fuel storage tank and the fuel dispenser. The fuel analyzer includes an ultrasonic transmitter configured to transmit an ultrasonic signal through a volume of the fuel, an ultrasonic receiver configured to receive the ultrasonic signal, and processing circuitry. The processing circuitry is configured to receive an indication of transmission of the ultrasonic signal from the ultrasonic transmitter, receive an indication of receipt of the ultrasonic signal from the ultrasonic receiver, determine a time of flight of the ultrasonic signal, and determine a fuel purity based on the time of flight of the ultrasonic signal.

Those skilled in the art will appreciate the scope of the present invention and realize additional aspects thereof after reading the following detailed description of preferred embodiments in association with the accompanying drawing figures.

BRIEF DESCRIPTION OF THE DRAWINGS

A full and enabling disclosure of the present invention, including the best mode thereof directed to one skilled in the art, is set forth in the specification, which makes reference to the appended drawings, in which:

FIG. 6 illustrates a method of utilizing a fuel analyzer according to an example embodiment of the present invention.

DETAILED DESCRIPTION OF PREFERRED EMBODIMENTS

Figure 1:
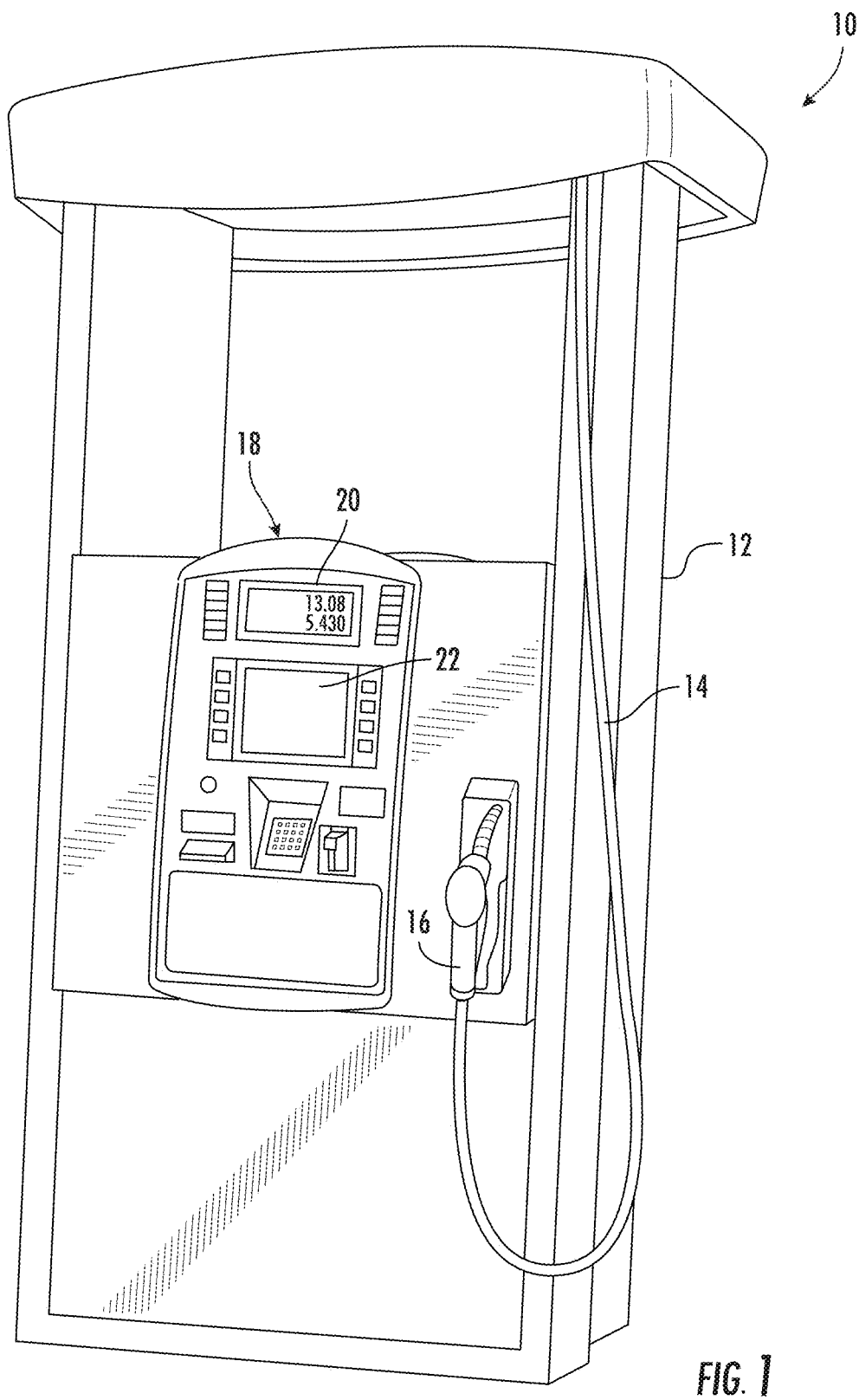
FIG. 1 illustrates a perspective view of an exemplary fuel dispenser in accordance with an embodiment of the present invention.

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the present disclosure including the appended claims and their equivalents.

The speed of sound traveling through a volume of fuel may change due to a change in the composition of the fuel, e.g. by adulteration of the fuel. This change in the speed of sound in the fuel is based on the change in density. In some examples, the change in speed of sound through the fuel may be substantial for a relatively small change in density. This relationship between the change in speed of sound in the fuel and the change in density of the fuel may be utilized to accurately measure adulteration of the fuel, by even a small amount, such as 1 percent, 2 percent, or the like.

In an example embodiment, a fuel analyzer including an ultrasonic transmitter and ultrasonic receiver may be disposed in the fuel system to measure the purity of the fuel and cause an alert or stop fuel flow in an instance in which the purity of the fuel fails to meet one or more purity thresholds. The alert may allow a user to identify and correct fuel sources which have become adulterated due to fraud, infrastructure issues, or human error. Additionally or alternatively, stopping the fuel flow may prevent or limit dispensing of adulterated fuel, which may cause damage to vehicle engines and not be of the value for which the customer is paying.

In some instances the fuel analyzer may be in communication with remote computing systems, which may allow for remote monitoring of fuel purity of one or more fueling environments. The remote monitoring of multiple fueling environments may allow a user to identify and correct fuel sources which have become adulterated due to fraud, infrastructure issues, or human error.

In an example embodiment, the fuel analyzer may be disposed in a bypass line, such that the measurement of the speed of sound through the fuel is not compromised by noise factors of the fueling operation, e.g. the flow of fuel through the fuel piping.

In some embodiments, the speed of sound and/or density expected for the fuel may be compensated for temperature and/or grade of fuel. In an example embodiment, the fuel analyzer may also be configured to measure ionic contaminants in the fuel, such as by an induction coil.

Some embodiments of the present invention may be particularly suitable for use with a fuel dispenser in a retail service station environment, and the below discussion will describe some preferred embodiments in that context. However, those of skill in the art will understand that the present invention is not so limited. In fact, it is contemplated that embodiments of the present invention may be used with any suitable fluid dispensing environment and with other fluid dispensers. For example, embodiments of the present invention may also be used with diesel exhaust fluid (DEF) dispensers.

Example Fuel Dispenser

FIG. 1 is a perspective view of an exemplary fuel dispenser 10 according to an embodiment of the present invention. Fuel dispenser 10 includes a housing 12 with a flexible fuel hose 14 extending therefrom. Fuel hose 14 terminates in a fuel nozzle 16 adapted to be inserted into a fill neck of a vehicle's fuel tank. Fuel nozzle 16 includes a manually-operated fuel valve. Various fuel handling components, such as valves and meters, are also located inside of housing 12. These fuel handling components allow fuel to be received from underground piping and delivered through fuel hose 14 and fuel nozzle 16 to a vehicle's fuel system, e.g. fuel tank.

Fuel dispenser 10 has a customer interface 18. Customer interface 18 may include an information display 20 relating to an ongoing fueling transaction that includes the amount of fuel dispensed and the price of the dispensed fuel. Further, customer interface 18 may include a display 22 that provides instructions to the customer regarding the fueling transaction. Display 22 may also provide advertising, merchandising, and multimedia presentations to a customer, and may allow the customer to purchase goods and services other than fuel at the dispenser. In some example embodiments, the customer interface may also include one or more fuel grade selectors.

Figure 2:
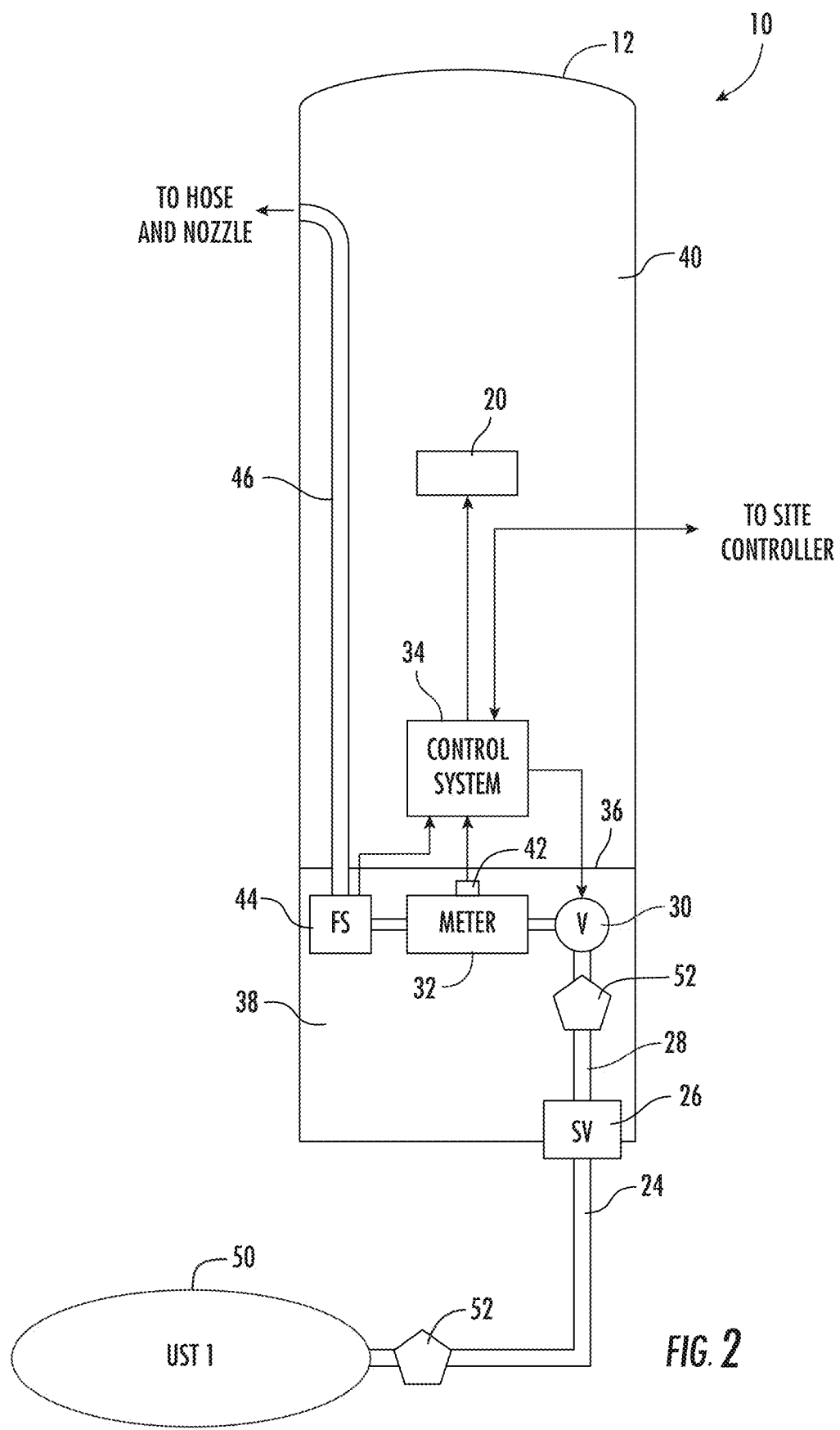
FIG. 2 illustrates a diagrammatic representation of internal components of the fuel dispenser of FIG. 1 according to an embodiment of the present invention.

FIG. 2 is a schematic illustration of internal fuel flow components of fuel dispenser 10 according to an embodiment of the present invention. In general, fuel may travel from one or more underground storage tanks (USTs) 50 via main fuel piping 24, which may be a double-walled pipe having secondary containment as is well known, to fuel dispenser 10 and nozzle 16 for delivery. An exemplary underground fuel delivery system is illustrated in U.S. Pat. No. 6,435,204, hereby incorporated by reference in its entirety for all purposes. More specifically, a submersible turbine pump (STP) associated with the UST is used to pump fuel to the fuel dispenser 10. However, some fuel dispensers may be self-contained, meaning fuel is drawn to the fuel dispenser 10 by a pump unit positioned within housing 12.

Main fuel piping 24 passes into housing 12 through a shear valve 26. As is well known, shear valve 26 is designed to close the fuel flow path in the event of an impact to fuel dispenser 10. U.S. Pat. No. 8,291,928, hereby incorporated by reference in its entirety for all purposes, discloses an exemplary secondarily-contained shear valve adapted for use in service station environments. Shear valve 26 contains an internal fuel flow path to carry fuel from main fuel piping 24 to internal fuel piping 28.

Fuel from the shear valve 26 flows toward a flow control valve 30 positioned upstream of a flow meter 32. Alternatively, flow control valve 30 may be positioned downstream of the flow meter 32. In one embodiment, flow control valve 30 may be a proportional solenoid controlled valve, such as described in U.S. Pat. No. 5,954,080, hereby incorporated by reference in its entirety for all purposes.

Flow control valve 30 is under control of a control system 34. In this manner, control system 34 can control the opening and closing of flow control valve 30 to either allow fuel to flow or not flow through meter 32 and on to the hose 14 and nozzle 16. Control system 34 may comprise any suitable electronics with associated memory and software programs running thereon whether referred to as a processor, microprocessor, controller, microcontroller, or the like. In a preferred embodiment, control system 34 may be comparable to the microprocessor-based control systems used in CRIND (card reader in dispenser) type units sold by Gilbarco Inc. Control system 34 typically controls other aspects of fuel dispenser 10, such as valves, displays, and the like. For example, control system 34 typically instructs flow control valve 30 to open when a fueling transaction is authorized. In addition, control system 34 may be in electronic communication with a point-of sale system (site controller) located at the fueling site. The site controller communicates with control system 34 to control authorization of fueling transactions and other conventional activities.

A vapor barrier 36 delimits hydraulics compartment 38 of fuel dispenser 10, and control system 34 is located in electronics compartment 40 above vapor barrier 36. Fluid handling components, such as flow meter 32, are located in hydraulics compartment 38. In this regard, flow meter 32 may be any suitable flow meter known to those of skill in the art, including positive displacement, inferential, and Coriolis mass flow meters, among others. Meter 32 typically comprises electronics 42 that communicates information representative of the flow rate or volume to control system 34. For example, electronics 42 may typically include a pulser as known to those skilled in the art. In this manner, control system 34 can update the total gallons (or liters) dispensed and the total price of the fuel dispensed on information display 20.

As fuel leaves flow meter 32 it enters a flow switch 44, which preferably comprises a one-way check valve that prevents rearward flow through fuel dispenser 10. Flow switch 44 provides a flow switch communication signal to control system 34 when fuel is flowing through flow meter 32. The flow switch communication signal indicates to control system 34 that fuel is actually flowing in the fuel delivery path and that subsequent signals from flow meter 32 are due to actual fuel flow. Fuel from flow switch 44 exits through internal fuel piping 46 to fuel hose 14 and nozzle 16 for delivery to the customer's vehicle.

A blend manifold may also be provided downstream of flow switch 44. The blend manifold receives fuels of varying octane levels from the various USTs and ensures that fuel of the octane level selected by the customer is delivered. In addition, fuel dispenser 10 may comprise a vapor recovery system to recover fuel vapors through nozzle 16 and hose 14 to return to the UST. An example of a vapor recovery assist equipped fuel dispenser is disclosed in U.S. Pat. No. 5,040,577, incorporated by reference herein in its entirety for all purposes.

In an example embodiment, one or more fuel analyzers 52 may be disposed in the fuel piping, e.g. main fuel piping 24 and/or internal fuel piping 28. For example, the fuel analyzer 52 may be disposed in the main fuel piping 24 at the outlet of the UST 50, such that the fuel analyzer 52 may determine a fuel purity of the fuel directly from the UST 50, which may identify adulteration of the fuel specific to the UST 50. Additionally or alternatively, the fuel analyzer 52 may be disposed in the internal fuel piping 28 in the hydraulics compartment 38. The fuel analyzer 52 may be disposed in the internal fuel piping 28 prior to the flow control valve 30 and/or the flow meter 32, such that a volume of fuel used for determination of fuel purity is not reflected by the flow meter 32 and therefore not charged to a customer. In some example embodiments, the fuel analyzer 52 may be disposed to measure the purity of fuel sources as the fuel enters the dispenser, or may be configured to monitor the purity of the fuel after two or more fuel types are blended to generate the selected fuel grade. The fuel analyzer 52 is discussed in further detail below in reference with FIGS. 3 and 4.

Example Fuel Analyzer

Figure 3:
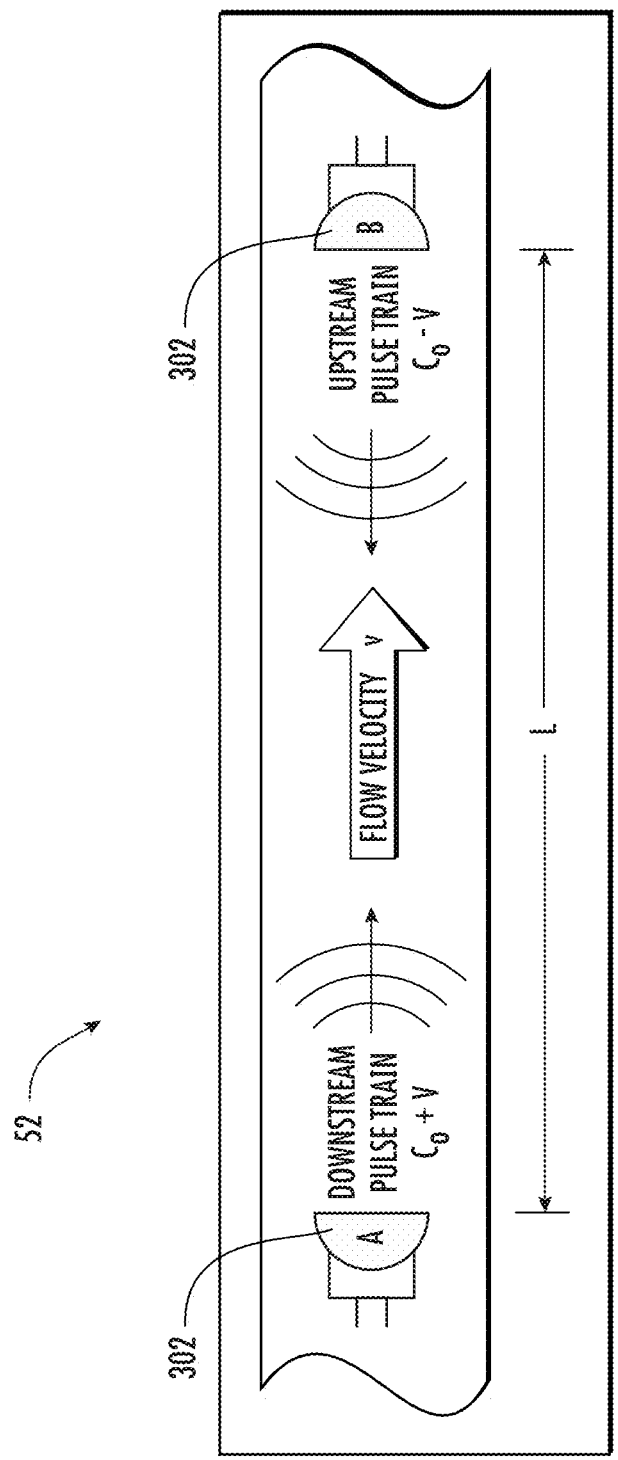
FIG. 3 illustrates aspects of an example fuel analyzer according to an embodiment of the present invention.

FIG. 3 Illustrates an example fuel analyzer 52 according to an example embodiment. The fuel analyzer may include two ultrasonic sensors 302. The ultrasonic sensors 302 may include at least one sensor transmitter and at least one sensor receiver. Additionally or alternatively, the ultrasonic sensors 302 may be ultrasonic transceivers configured to transmit and/or receive the ultrasonic signal.

A speed of sound (SoS) through a volume of fuel may be measured by calculating the time of flight (ToF) of an ultrasound wave packet from position A to position B, where A and B have mounted an ultrasound transceiver. The distance between position A and position B may define a length (L). For (v=0) conditions, e.g. fluid not moving, the SoS may be measured as:

$$SoS = L/ToF \qquad \text{EQN. 1}$$

The fuel analyzer 52 may be configured such that the sending and receiving ultrasonic sensors 302 are as far apart as possible, for example at the opposite ends of a rectangle or cylinder vessel. In an example embodiment, a rectangular vessel may be configured such that the sending ultrasonic sensor 302 is mounted just over the fuel inlet, and receiving ultrasonic sensor 302 is just below the outlet, allowing for straight line excitation between sending and receiving ultrasonic sensors 302. An extended length between the sending ultrasonic sensor 302 and receiving ultrasonic sensor 302 reduces the effects of manufacturing tolerance errors or temperature based shape changes on the fuel purity measurement. For example, a typical value of speed of sound in pure diesel is about 1300 m/s. If L=10 cm, ToF may be a relatively small value, such as 77 microseconds. A 1 percent error in the length (L) may be sufficient to cause an incorrect purity measurement of same fuel. However, the longer the length (L) the lower the measurement error.

The SoS through the fuel volume may change with a change in density of the fuel. A typical gasoline density may be 0.71-0.77 g/cm$^3$, however the density of typical adulterants is higher. Since, the adulterants have a higher density than gasoline, the density of the adulterated fuel may be higher than the pure fuel resulting in a shorter ToF.

The speed and direction of fuel flow may also effect the SoS and therefore ToF. ToF A to B may be different from ToF B to A, due to the velocity of the fuel. If flow is from A to B, as depicted, ToF A to B will be much shorter than ToF B to A.

$$\text{ToF } A \text{ to } B = L/(\text{Velocity of Sound} + \text{Velocity of Fuel}) \qquad \text{EQN. 2}$$

$$\text{ToF } B \text{ to } A = L/(\text{Velocity of Sound} - \text{Velocity of Fuel}) \qquad \text{EQN. 3}$$

The fuel analyzer 52 may be calibrated at a nominal temperature, such as 75 degrees Fahrenheit using a nominal calibration fluid, such as distilled water with a density of 1 g/cm$^3$. A calibration table may be generated by determining L between A and B at various temperatures, to compensate for variations due to temperature. The ambient temperature at the dispenser 10 may be determined from a sensor associated with the dispenser 10 or the fueling environment. Additionally or alternatively, the ambient temperature may be received from a weather service or weather database. The fuel analyzer 52 may determine the correct L between A and B from the calibration table based on the received ambient temperature.

A second calibration table may be developed for each grade of fuel to be dispensed including expected ToFs established as a function of temperature. Each calibration table may be stored to a memory for comparison during fueling operations.

In some example embodiments, one or more purity thresholds may be set. A first purity thresholds may be utilized by dispenser operators to monitor their fuel deliveries and for notifying suppliers that they may be on the verge of providing unusable fuel. The first purity threshold may be 99 percent, 98 percent, or the like. A second purity threshold, which is lower than the first purity threshold, such as 95 percent 90 percent, or the like, may be utilized to stop fuel dispensing, as discuss below. In some instances, fuel purity may be provided to the customer interface 18, such that the end user can be assured that the fuel quality is acceptable, and to draw comparisons to other fuel vendors.

Figure 4:
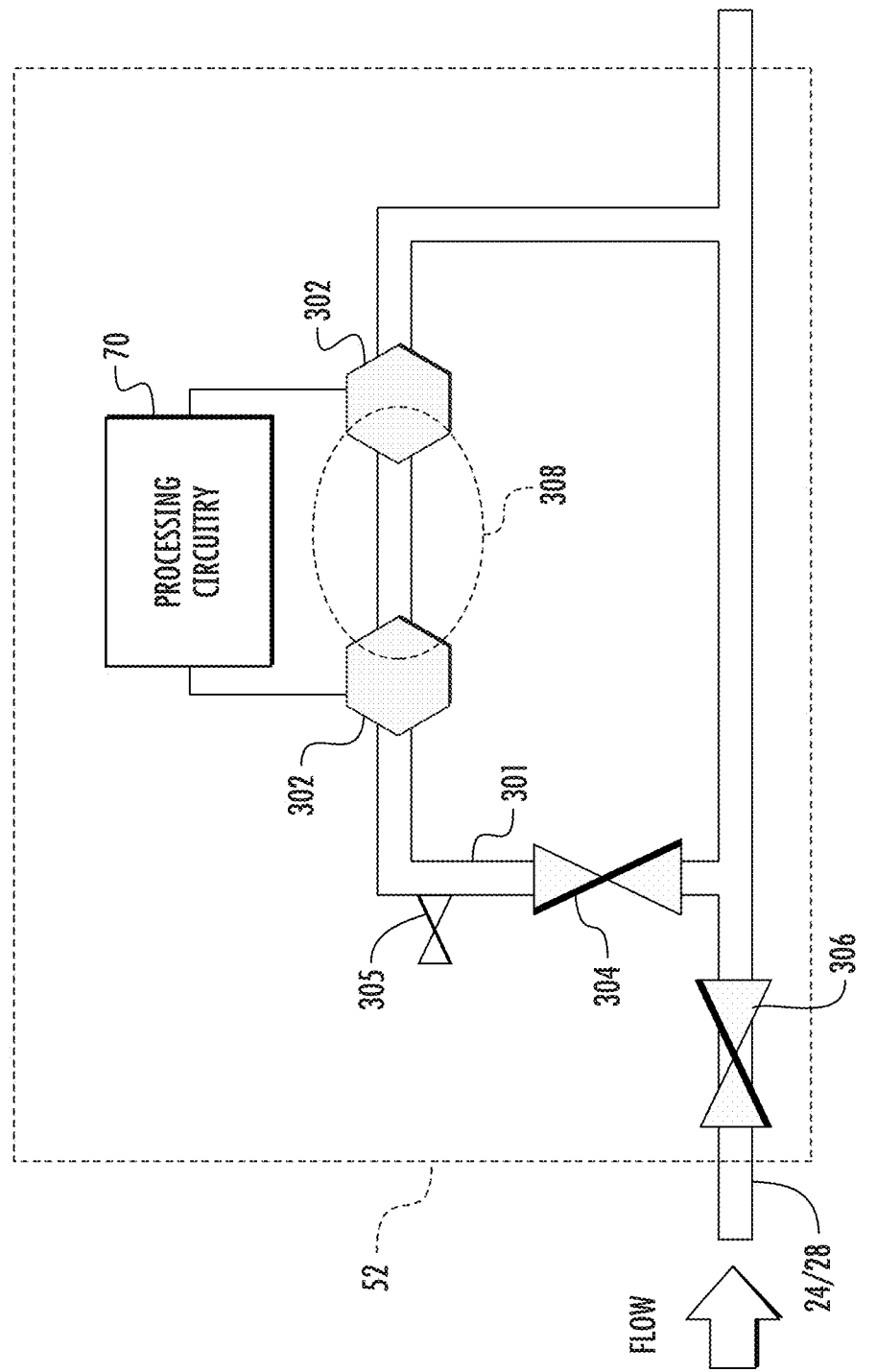
FIG. 4 illustrates aspects of an example fuel analyzer in a fuel piping bypass according to an example embodiment.

FIG. 4 illustrates an example fuel analyzer 52 disposed in a fuel piping bypass 301 according to an example embodiment. The fuel analyzer 52 may include the first and second ultrasonic sensors 302 and processing circuitry 70. The processing circuitry 70 may be dedicated processing circuitry associated with the fuel analyzer 52 or may be a portion of the control system 34.

The fuel analyzer 52 may be disposed in the fuel piping 24, 28 or may be disposed in a fuel piping bypass 301. Disposing the fuel analyzer 52 in a fuel piping bypass 301 may allow for the fuel dispensing to be unobstructed preventing slowing of the fuel dispensing velocity. Additionally, the fuel analyzer 52 disposed in the fuel piping bypass 301 may enable the volume of fuel to be isolated from the fuel flow, thereby limiting or preventing flow related noise, variation due to flow rate, and compensation requirements. Since, the fuel dispensing is unobstructed and the volume of fuel being measured is isolated the fuel purity may be determined dynamically as the fuel is dispensed, in contrast to a static measurement before or after fueling.

Figure 5:
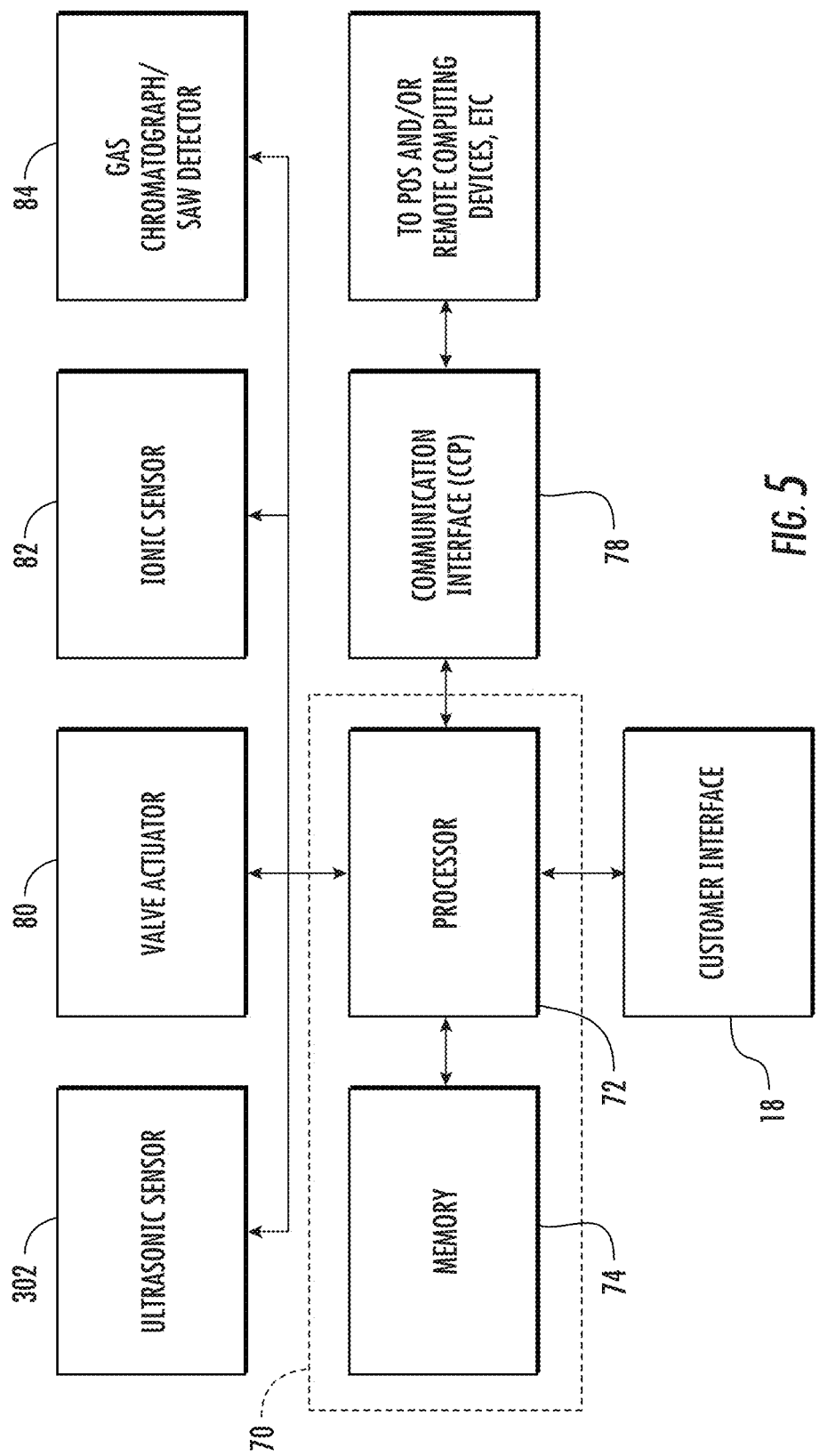
FIG. 5 illustrates a block diagram of one example of processing circuitry according to an embodiment of the present invention.

In an example embodiment, additional sensors 308 may be incorporated into the fuel analyzer 52. For example, an ionic sensor 82, as depicted in FIG. 5, may be utilized to determine ionic contaminants. The ionic sensor 82 may include a magnetic or induction coil disposed, e.g. wrapped, around the fuel piping bypass, or other piping in which the fuel analyzer is disposed. The processing circuitry 70 may store a third calibration table for each fuel type or grade, which may be compared to the ionic signature of the fuel volume. The processing circuitry 70 may also determine if the ionic signature falls within one or more acceptable ranges or ionic signature thresholds. For example, a first ionic threshold, such as 99 percent, 98 percent, or the like may be utilized by dispenser operators to monitor their fuel deliveries and for notifying suppliers that they may be on the verge of providing unusable fuel and a second ionic threshold, which is lower than the first purity threshold, such as 95 percent 90 percent, or the like, may be utilized to stop fuel dispensing. In some example embodiments, the ionic contamination measurement may be incorporated into the fuel purity, such as a weighted average or an adjustment factor applied to the fuel purity.

In some example embodiments, the additional sensor 308 may include a gas chromatograph/surface acoustic wave (SAW) detector 84. In some instances the gas chromatograph/SAW detector 84 may be used as a calibration source, such as at the UST 50 output that feeds one or more dispensers 10. A fuel analyzer 52 equipped with the gas chromatograph/SAW detector 84 may be utilized to develop a calibration table for the output fuel and by connecting the fuel analyzer 52 to a remote computing device, automatic calibration tables can be generated and transmitted to each fuel analyzer 52 of the one or more dispensers 10, for each delivery of any fuel type or grade. Furthermore, the fuel analyzer 52 disposed at the output of the UST 50 may be correlated with each fuel analyzer 52 disposed in the one or more dispensers 10, to detect potential issues in the distribution piping on the forecourt, such as leaks or improper connections, causing adulterations to occur in the distribution chain.

In operation, the fuel analyzer 52 may be operably coupled in the fuel piping 24, 28, such that the fuel flows through the fuel analyzer 52. The fuel analyzer 52 may include the fuel piping bypass 301 in which the first and second ultrasonic sensors 302 are disposed. The fuel piping bypass 301 may include a sample valve 304 configured to be opened by the processing circuitry 70 to obtain a volume of fuel for purity measurement. In some example embodiments, the sample valve 304 may be shut for a purge period, such as 2, seconds, 3, seconds 5 seconds, or the like, to allow fuel from a previous fueling operation to be evacuated prior to obtaining the volume of fuel.

The processing circuitry 70 may cause the sample valve 304 to open allowing fuel to flow through the fuel bypass piping 301. In an example embodiment in which a fuel velocity is available, such as by a flow rate sensor, the sample valve 304 may remain open and the following analysis may be performed dynamically. In some example embodiments, the processing circuitry 70 may cause the sample valve to shut to perform the analysis with no fuel flow in the fuel piping bypass 301. In further example embodiments, the processing circuitry 70 may cycle the sample valve 304 multiple times during a fueling operation to perform the following analysis a plurality of times over the duration of the fueling operation.

Once the volume of fuel has been captured in the fuel piping bypass 301, the SoS measurement may be performed to determine the ToF, with v=0 for the sample valve closed with EQN. 1 above, or dynamically with EQN. 2 and/or EQN. 3 above with a v based on flow rate of the fuel. The processing circuitry 70 may receive an indication of transmission of the ultrasonic signal from the first ultrasonic sensor 302 and an indication of receipt of the ultrasonic signal from the second ultrasonic sensor 302. The indication of transmission or indication of receipt may include a time stamp or the processing circuitry 70 may generate a time stamp upon receipt or the respective indications. In some embodiments, a second valve 304 may be located at the downstream portion of bypass 301 to trap and further isolate the fuel to be analyzed.

The processing circuitry 70 may determine a difference between the time stamp associated with the indication of transmission and the time stamp associated with the indication of receipt to determine a ToF, such as 80 microseconds. The ToF may be compared to an expected ToF, such as from a calibration table. The difference between the ToF and the expected ToF may be indicative of the purity of the volume of fuel.

In some example embodiments, the processing circuitry 70 may receive an indication of ambient temperature. The processing circuitry 70 may use a temperature compensated value of the expected ToF to determine the purity of the volume of fuel and/or compensate the ToF value based on the ambient temperature.

In an example embodiment, the processing circuitry 70 may receive an indication of a selected fuel grade. The processing circuitry 70 may compare the ToF with an expected ToF which is calibrated for the selected fuel grade to determine the purity of fuel.

In some example embodiments, the processing circuitry 70 may receive an indication of the ionic contaminates from the ionic sensor 82. The indication of ionic contaminates may be an ionic or magnetic signature of the fuel volume in the fuel analyzer 52. The processing circuitry 70 may compare the ionic signature of the volume of fuel to a calibration table for the fuel or selected fuel grade to determine an ionic impurity. The ionic impurity may be compared to an allowable impurity threshold, such as 100 ppb, 200 ppb, or the like. In some instances, a value may be assigned to the commination impurity, such as 0.99, 0.98 or the like, which may be used an adjustment factor to the determined purity of the volume of fuel.

In an example embodiment, the processing circuitry 70 may cause the fuel purity to be displayed on the customer interface 18, such as during the fueling operation, after the fueling operation, or the like.

In an example embodiment, the processing circuitry 70 may determine a difference between the fuel purity, or the ionic impurity adjusted fuel purity, and an expected fuel purity. The expected fuel purity may be 100 percent, or may include an error margin such as 1 percent, to prevent false positives for adulteration of the fuel. The processing circuitry 70 may compare the difference between the fuel purity and the expected fuel purity to one or more purity thresholds. In some example embodiments, a first purity threshold, such as 2 percent, 5 percent, or the like which corresponds to 98 percent and 95 percent purity respectively, may be utilized by dispenser operators to monitor their fuel deliveries and for notifying suppliers that they may be on the verge of providing unusable fuel. A second purity threshold, which is higher than the first purity threshold, such as 10 percent or 15 percent corresponding to 90 percent and 85 percent fuel purity respectively, may be utilized to stop fuel dispensing.

In some example embodiments, such as in response to the fuel purity exceeding the first purity threshold or second purity threshold, the processing circuitry 70 may cause an alert. The alert may be a visual indication, such as a buzzer, siren, horn, beep, or the like, or the alert may be a visual indication, such as a flashing light strobe light, blinking light, textual message or the like to indicate to a user or operator that a purity threshold has been exceeded. The alert may be at the dispenser 10, in a convenience store associated with the fueling environment, a remote computing device, or the like. In an example embodiment, fuel purity values from multiple fueling environments may be tracked by the remote computing device allowing prediction of adulteration of fuel in geographical areas.

In an example embodiment, the processing circuitry 70 may be configured to cause a flow control valve to shut. The flow control valve may be a fuel analyzer flow control valve 306 disposed in the fuel analyzer 52 or may be the flow control valve 30 associated with the dispenser 30. The flow control valve 306, 30 may be shut in response to the processing circuitry 70 determining that the purity threshold has been exceeded. In some example embodiments, the processing circuitry 70 may close or maintain closed the sample valve 304 to trap the fuel volume for further testing after an alert or after a fuel cutoff. The volume of fuel may be drained via a purge valve 305 operably coupled to the fuel analyzer 52, e.g. the fuel piping bypass 301.

Example Processing Circuitry

FIG. 5 shows certain elements of processing circuitry 70 according to an example embodiment. The processing circuitry 70 of FIG. 5 may be employed, for example, on onboard circuitry within the fuel analyzer 52, in circuitry associated with the control system 34, a convenience store, a network device, server, proxy, or the like. Alternatively, embodiments may be employed on a combination of devices. Furthermore, it should be noted that the devices or elements described below may not be mandatory and thus some may be omitted in certain embodiments.

In an example embodiment, processing circuitry 70 is provided configured to perform data processing, application execution and other processing and management services according to an example embodiment of the present invention. In one embodiment, the processing circuitry 70 may include a memory 74 and a processor 72 that may be in communication with or otherwise control a customer interface 18 and/or communication interface 78. As such, the processing circuitry 70 may be embodied as a circuit chip (e.g. an integrated circuit chip) configured (e.g. with hardware, software or a combination of hardware and software) to perform operations described herein. However, in some embodiments, the processing circuitry 70 may be embodied as a portion of a server, computer, or workstation. The network may be a data network, such as a local area network (LAN), a metropolitan area network (MAN), a wide area network (WAN) (e.g. the Internet), and/or the like, which may couple the processing circuitry 70, the control system 34, and/or the fuel dispenser 10 to devices such as processing elements (e.g. computer terminals, server computers or the like) and/or databases. Communication between the network, the processing circuitry 70, the control system 34, and the devices or databases (e.g. servers) to which the processing circuitry 70 is coupled may be accomplished by either wireline or wireless communication mechanisms and corresponding communication protocols.

The customer interface 18 may be an input/output device for receiving instructions directly from a user. The customer interface 18 may be in communication with the processing circuitry 70 to receive user input via the customer interface 18 and/or to present output to a user as, for example, audible, visual, mechanical or other output indications. The customer interface 18 may include, for example, a keyboard, a mouse, a joystick, a display (e.g. a touch screen display), a microphone, a speaker, or other input/output mechanisms. Further, the processing circuitry 70 may comprise, or be in communication with, user interface circuitry configured to control at least some functions of one or more elements of the customer interface 18. The processing circuitry 70 and/or user interface circuitry may be configured to control one or more functions of one or more elements of the user interface 26 through computer program instructions (e.g. software and/or firmware) stored on a memory device accessible to the processing circuitry 70 (e.g. volatile memory, non-volatile memory, and/or the like). In some example embodiments, the user interface circuitry is configured to facilitate user control of at least some functions of the apparatus through the use of a display configured to respond to user inputs. The processing circuitry 70 may also comprise; or be in communication with, display circuitry configured to display at least a portion of a customer interface 18, the display and the display circuitry configured to facilitate user control of at least some functions of the apparatus.

The communication interface 78 may be any means such as a device or circuitry embodied in either hardware, software, or a combination of hardware and software that is configured to receive and/or transmit data from/to a network and/or any other device or module in communication with the control system 34 and/or the POS of the fueling environment (and/or a remote cloud server, either directly or via a router located in the convenience store). In some instances the communications interface 78 may be referred to as a cloud connection processor (CCP) and may provide secured, e.g. encrypted, communication between the processing circuitry 70, the network, and/or remote servers or remote computing devices. The communication interface 78 may also include, for example, an antenna (or multiple antennas) and supporting hardware and/or software for enabling communications with the network or other devices (e.g. a user device). In some environments, the communication interface 78 may alternatively or additionally support wired communication. As such, for example, the communication interface 78 may include a communication modem and/or other hardware/software for supporting communication via cable, digital subscriber line (DSL), universal serial bus (USB) or other mechanisms. In an exemplary embodiment, the communication interface 78 may support communication via one or more different communication protocols or methods. In some cases, IEEE 802.15.4 based communication techniques such as WiFi, ZigBee, Bluetooth, or other low power, short range communication protocols, such as a proprietary technique based on IEEE 802.15.4 may be employed along with radio frequency identification (RFID) or other short range communication techniques.

The processing circuitry 70 may include or otherwise be in communication with the ultrasonic sensors 302. The ultrasonic sensors 302 may include a sensor transmitter configured to transmit an ultrasonic signal though a volume of fuel and a sensor receiver configured to receive the ultrasonic signal. The ultrasonic signal may be an ultrasonic waveform, an ultrasonic digital packet, or the like, configured to pass through the volume of fuel and be received by the sensor receiver. In an example embodiment, the sensor receiver and/or the sensor transmitter may be an ultrasonic transceiver.

In some example embodiments, the processing circuitry 70 may also include or otherwise be in communication with a valve actuator 80 of the flow control valve 30 or the valves 304 and 306. The valve actuator may include the magnetic coil and plunger, a servo motor, a power transistor, or other device to control the position of the flow control valve 30 or the fuel analyzer flow control valve 306. The processing circuitry 70 may cause the valve actuator 80 to cause the flow control valve 30 or fuel analyzer flow control valve 306 to shift between the open position and the shut position to capture the volume of fuel for ultrasonic analysis, as described above. Additionally or alternatively, the processing circuitry 70 may determine if the fuel purity is within one or more purity thresholds and cause the flow control valve 30 or the fuel analyzer flow control valve 306 to shift to the shut position in response to determining the that the difference between the fuel purity and the expected fuel purity exceeds the purity threshold.

In an example embodiment, the processing circuitry 70 may include or otherwise be in communication with an ionic sensor 82. The ionic sensor 82 may include a magnetic or induction coil disposed around a fuel conduit, e.g. fuel piping bypass 301. In some instances fuel conduit may be formed from a non-metallic material, such as plastic, rubber, or the like. The induction coil may measure a change in the magnetic field due to ionic impurities in the fuel, e.g. an ionic signature. The fuel purity may be further based on the measure of ionic impurities, such as by applying an adjustment factor to the determined fuel purity based on the ionic impurities.

In some example embodiments, the processing circuitry 70 may include or otherwise be in communication with a gas chromatograph/SAW detector 84, such as in fuel analyzer 52 disposed at the output of a UST 50. The gas chromatograph/SAW detector 84 may be configured to provide mass and/or molecular analysis of the fuel. The molecular analysis of the fuel may be used to generate a calibration table for the fuel to be used fuel analyzers 52 disposed in one or more dispensers 10 of a fueling environment.

Example Flowchart(s) and Operations

Embodiments of the present invention provide methods, apparatus and computer program products for fuel cutoff using a fuel flow control valve. Various examples of the operations performed in accordance with embodiments of the present invention will now be provided with reference to FIG. 6.

FIG. 6 illustrates flowchart according to an example method for fuel cutoff using a fuel flow control valve according to an example embodiment. The operations illustrated in and described with respect to FIG. 6 may, for example, be performed by, with the assistance of, and/or under the control of one or more of the processor 72, memory 74, communication interface 78, ultrasonic sensor 302, ionic sensor 504, and/or the valve actuator 502. The method depicted in FIG. 6 may include receiving an indication of transmission of the ultrasonic signal at operation 606, receiving an indication of receipt of the ultrasonic signal at operation 608, determining a time of flight of the ultrasonic signal at operation 610, and determining a fuel purity based on the time of flight of the ultrasonic signal at operation 614.

In some embodiments, the method may include additional, optional operations, and/or the operations described above may be modified or augmented. Some examples of modifications, optional operations, and augmentations are described below, as indicated by dashed lines, such as, receiving an indication of ambient temperature at operation 602 and receiving an indication of fuel grade at operation 604. In an example embodiment, the method may also include comparing the time of flight to an expected time of flight at operation 612, receiving an indication of ionic contaminates from an ionic contamination sensor at operation 614, and causing the fuel purity to be displayed on a customer interface at operation 615. In some example embodiments the method may also include determining a difference between the fuel purity and an expected fuel purity at operation 618, comparing the difference between the fuel purity and an expected fuel purity to a purity threshold at operation 620, causing an alert based on the difference between the fuel purity and the expected fuel purity exceeding the purity threshold at operation 622, and causing a flow control valve to shut based on the difference between the fuel purity and the expected fuel purity exceeding the purity threshold at operation 624.

FIG. 6 illustrates a flowchart of a system, method, and computer program product according to an example embodiment. It will be understood that each block of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by, for example, the memory 74 and executed by, for example, the processor 72. As will be appreciated, any such computer program product may be loaded onto a computer or other programmable apparatus (for example, the processing circuitry of the fuel flow control valve) to produce a machine, such that the computer program product including the instructions which execute on the computer or other programmable apparatus creates means for implementing the functions specified in the flowchart block(s). Further, the computer program product may comprise one or more non-transitory computer-readable mediums on which the computer program instructions may be stored such that the one or more computer-readable memories can direct a computer or other programmable device to cause a series of operations to be performed on the computer or other programmable apparatus to produce a computer-implemented process such that the instructions which execute on the computer or other programmable apparatus implement the functions specified in the flowchart block(s).

In some embodiments, the dispenser may be further configured for additional operations or optional modifications. In this regard, in an example embodiment, the time of flight is based on the density of the fuel. In an example embodiment, the fuel analyzer is disposed in a bypass line of fuel piping. In some example embodiments, the processing circuitry is further configured to compare the time of flight to an expected time of flight and the fuel purity is based on a difference between the time of flight and the expected time of flight. In an example embodiment, the processing circuitry is further configured to receive an indication of ambient temperature and the expected time of flight is based on the ambient temperature. In some example embodiments, the processing circuitry is further configured to receive an indication of fuel grade and the expected time of flight is based on the fuel grade. In an example embodiment, the processing circuitry is further configured to determine a difference between the fuel purity and an expected fuel purity and compare the difference between the fuel purity and the expected fuel purity to a purity threshold. In some example embodiments, the processing circuitry is further configured to cause an alert based on the difference between the fuel purity and the expected fuel purity exceeding the purity threshold. In an example embodiment, the processing circuitry is further configured to cause a flow control valve to shut based on the difference between the fuel purity and the expected fuel purity exceeding the purity threshold. In some example embodiments, the fuel analyzer also includes an ionic contaminant sensor configured to detect ionic contaminates in the fuel.

Many modifications and other embodiments of the embodiment and/or methodology set forth herein will come to mind to one skilled in the art to which they pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the invention. In this regard, for example, different combinations of elements and/or functions than those explicitly described above are also contemplated within the scope of the invention. Although specific terms are employed herein, they are used in a generic and descriptive sense only and not for purposes of limitation.

What is claimed is:

1. A fuel analyzer for a fuel dispensing environment comprising:
    an ultrasonic transmitter configured to transmit an ultrasonic signal through a volume of fuel;
    an ultrasonic receiver configured to receive the ultrasonic signal; and
    processing circuitry configured to:
        receive an indication of transmission of the ultrasonic signal from the ultrasonic transmitter;
        receive an indication of receipt of the ultrasonic signal from the ultrasonic receiver;
        determine a time of flight of the ultrasonic signal; and
        determine a fuel purity based on the time of flight of the ultrasonic signal,
    wherein the processing circuitry is further configured to:
        determine a difference between the fuel purity and an expected fuel purity;
        compare the difference between the fuel purity and the expected fuel purity to a purity threshold; and
        cause an alert based on the difference between the fuel purity and the expected fuel purity exceeding the purity threshold.

2. The fuel analyzer of claim 1, wherein the fuel analyzer is disposed in a bypass line of fuel piping.

3. The fuel analyzer of claim 1, wherein the processing circuitry is further configured to:
    compare the time of flight to an expected time of flight, and
    wherein the fuel purity is based on a difference between the time of flight and the expected time of flight.

4. The fuel analyzer of claim 3, wherein the processing circuitry is further configured to receive an indication of ambient temperature, and wherein the expected time of flight is based on the ambient temperature.

5. The fuel analyzer of claim 3, wherein the processing circuitry is further configured to receive an indication of fuel grade, and
    wherein the expected time of flight is based on the fuel grade.

6. The fuel analyzer of claim 1, wherein the processing circuitry is further configured to:
    cause a flow control valve to shut based on the difference between the fuel purity and the expected fuel purity exceeding the purity threshold.

7. The fuel analyzer of claim 1, further comprising:
    an ionic contaminant sensor configured to detect ionic contaminates in the fuel.

8. A fuel dispenser comprising:
    a fuel nozzle configured to be connected to a vehicle fuel system,
    fuel piping configured to transfer fuel from at least one fuel storage tank associated with the fuel dispenser through the fuel nozzle into the vehicle fuel system; and
    a fuel analyzer comprising:
        an ultrasonic transmitter configured to transmit an ultrasonic signal through a volume of fuel;
        an ultrasonic receiver configured to receive the ultrasonic signal; and processing circuitry configured to:
receive an indication of transmission of the ultrasonic signal from the ultrasonic transmitter;
receive an indication of receipt of the ultrasonic signal from the ultrasonic receiver;
determine a time of flight of the ultrasonic signal; and
determine a fuel purity based on the time of flight of the ultrasonic signal,
wherein the processing circuitry is further configured to:
determine a difference between the fuel purity and an expected fuel purity;
compare the difference between the fuel purity and the expected fuel purity to a purity threshold; and
cause an alert based on the difference between the fuel purity and the expected fuel purity exceeding the purity threshold.

9. The fuel dispenser of claim 8, wherein the time of flight is based on the density of the fuel.

10. The fuel dispenser of claim 8, wherein the fuel analyzer is disposed in a bypass line of the fuel piping.

11. The fuel dispenser of claim 8, wherein the processing circuitry is further configured to:
compare the time of flight to an expected time of flight, and
wherein the fuel purity is based on a difference between the time of flight and the expected time of flight.

12. The fuel dispenser of claim 11, wherein the processing circuitry is further configured to receive an indication of ambient temperature, and
wherein the expected time of flight is based on the ambient temperature.

13. The fuel dispenser of claim 11, wherein the processing circuitry is further configured to receive an indication of fuel grade, and
wherein the expected time of flight is based on the fuel grade.

14. The fuel dispenser of claim 8, wherein the processing circuitry is further configured to:
cause a flow control valve to shut based on the difference between the fuel purity and the expected fuel purity exceeding the purity threshold.

15. The fuel dispenser of claim 8 further comprising:
an ionic contaminant sensor configured to detect ionic contaminates in the fuel.

\* \* \* \* \*